United States Patent [19]

Burcham

[11] 4,444,194

[45] Apr. 24, 1984

[54] MEDICAL ELECTRODE ASSEMBLY

[75] Inventor: Larry R. Burcham, Xenia, Ohio

[73] Assignee: NDM Corporation, Dayton, Ohio

[21] Appl. No.: 356,097

[22] Filed: Mar. 8, 1982

[51] Int. Cl.³ .............................................. A61B 5/04
[52] U.S. Cl. .................................................... 128/641
[58] Field of Search ............................... 128/639–641, 128/644, 798, 802, 803, 303.13

[56] References Cited

U.S. PATENT DOCUMENTS

| | | | |
|---|---|---|---|
| 3,085,577 | 4/1963 | Berman et al. | 128/2.06 E |
| 3,696,807 | 10/1972 | Szpur | 128/2.1 E |
| 3,701,346 | 10/1972 | Patrick et al. | 128/2.06 E |
| 3,713,435 | 1/1973 | Szpur | 128/2.06 E |
| 3,820,531 | 6/1974 | Szpur | 128/2.06 E |
| 3,830,229 | 8/1974 | Johnson | 128/2.06 E |
| 3,841,312 | 10/1974 | Corasanti | 128/2.06 E |
| 3,942,517 | 3/1976 | Bowles et al. | 128/2.1 E |
| 3,982,529 | 9/1976 | Sato | 128/2.06 E |
| 3,989,035 | 11/1976 | Zuehlsdorff | 128/2.1 E |
| 4,019,500 | 4/1977 | Patrick, Jr. et al. | 128/2.1 E |
| 4,029,086 | 6/1977 | Corasanti | 128/2.06 E |
| 4,040,412 | 8/1977 | Sato | 128/2.06 E |
| 4,114,263 | 9/1978 | Szpur | 29/630 R |
| 4,137,909 | 2/1979 | Hix | 128/2.06 E |
| 4,161,174 | 7/1979 | Mercuri | 128/641 |
| 4,226,247 | 10/1980 | Hauser et al. | 128/641 |
| 4,311,152 | 1/1982 | Modes et al. | 128/641 |

Primary Examiner—Lee S. Cohen
Attorney, Agent, or Firm—Roger S. Dybvig

[57] ABSTRACT

The eyelet of a snap fastener conductor extends both through an adhesively coated supporting sheet and a gel pad whereupon a flange on the eyelet cooperates with the gel pad to form a cup-like cavity in which electrolyte gel is placed. The supporting sheet is formed from a substantially moisture and water vapor impervious material and cooperates with a cover that is also substantially moisture and water vapor impervious having a cavity receiving the gel pad to prevent gel dry out. The gel pad receiving cavity has a centrally located plug that enters the cup-like cavity during assembly to displace the gel into adjacent portions of the gel pad and also to resist substantial movement of the snap fastener conductor when a lead wire is attached.

13 Claims, 4 Drawing Figures

U.S. Patent   Apr. 24, 1984   4,444,194
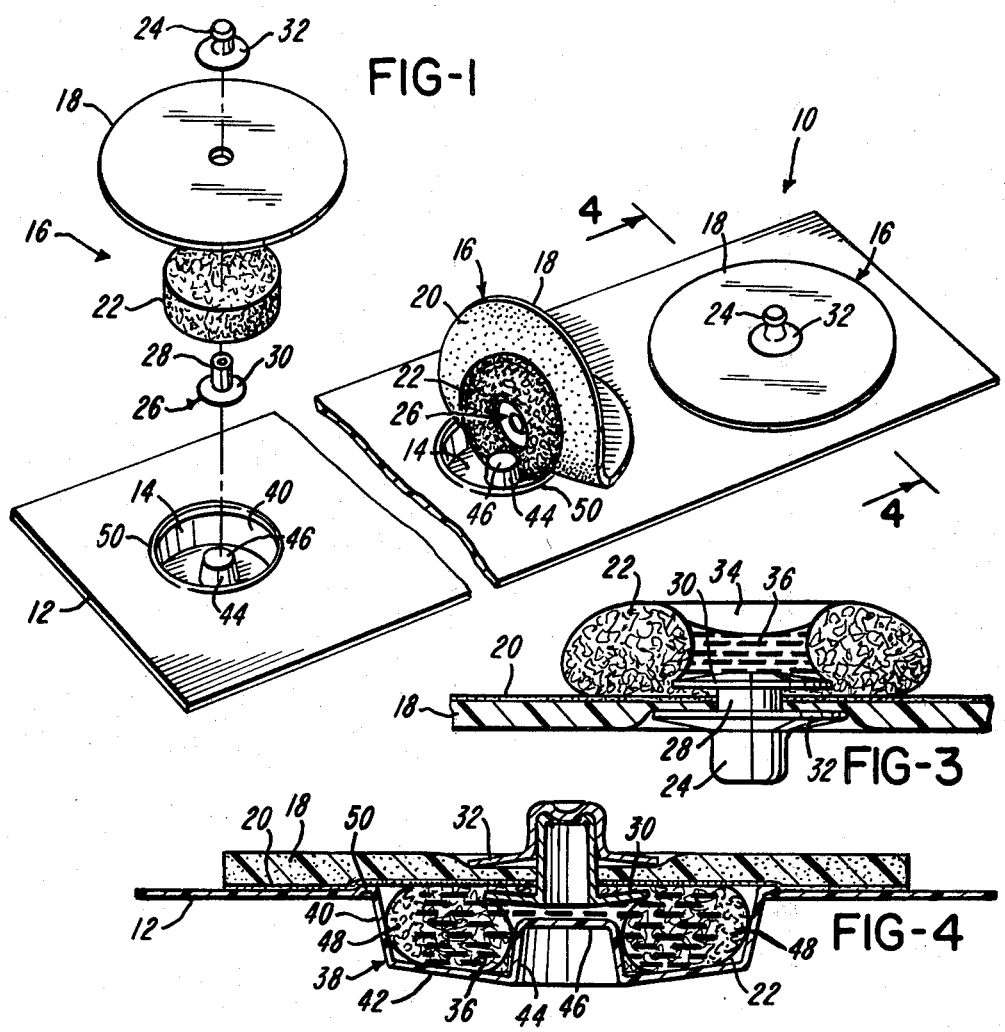
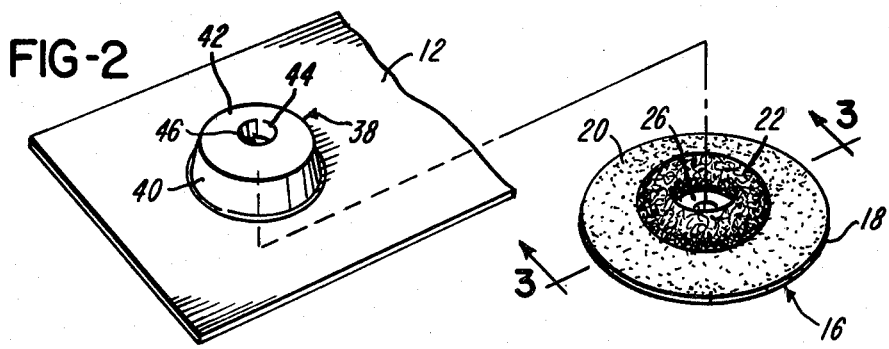

MEDICAL ELECTRODE ASSEMBLY

SUMMARY OF THE INVENTION

This invention relates to a medical electrode assembly and primarily to a medical electrode assembly for use in EKG testing procedures, although the invention may also be used in medical electrode assemblies generally for establishing an electrical connection between the skin of an animal, usually a human, and signal monitoring or signal applying devices of various types.

The invention is primarily directed to improvements in electrode assemblies having disposable, low-profile electrodes, that is, electrodes which have a relatively low height with respect to area of skin contact. In particular, the electrodes are of a type including an adhesively coated sheet for engaging the skin, an electrode conductor supported by the sheet, an electrolyte in the form of a gel for transmitting electrical signals between the conductor and the skin, and a foam gel pad loaded with the electrolyte. The primary purpose of the gel pad is to promote stability in the functioning of the electrolyte by insuring reasonably uniform and constant contact between the electrolyte and both the electrode conductor and the skin. The electrodes are known as "pre-filled" because the gel pad is filled with an electrolytic jelly during manufacture whereby the electrode is ready for immediate use as soon as it is unpackaged.

The electrodes of this invention are primarily intended for use in relatively short-term EKG testing in medical laboratories or doctor's offices. A common procedure involves the use of two sets of five electrodes each, or a total of ten electrodes, and if such electrodes are to be disposable, each electrode must be economically manufactured.

Many medical electrodes presently in use include an adhesively coated, skin contacting supporting sheet having a conductor in the form of a snap fastener element projecting through the supporting sheet and also through a relatively rigid cup member. The cup member, known as a "gel cup" engages the adhesive coating on the supporting sheet and receives a gel pad loaded with an electrolyte. Among other functions, the gel cup in many electrodes cooperates with an electrode cover structure to house the gel pad in a sufficiently water and air-tight chamber to prevent the gel pad from drying out over a prolonged period of time.

U.S. Pat. No. 3,701,346, issued to Charles T. Patrick, Jr. et al. shows an example of a low profile, disposable, pre-gelled medical electrode and a cover structure. The Patrick, Jr. et al. cover includes an inwardly projecting portion engaging a gel pad designed to maintain the gel pad in place in a gel cup while providing a sufficiently small area of contact with the gel pad that it will not tend to be removed from the gel cup when the cover structure is removed. More recently, medical electrodes with gel cups have been marketed which are provided with ribs or indentations that engage the rims of the gel cup. These cover structures are relatively rigid so that if, as is common practice, one would push a lead wire connector onto the connector portion of the electrode conductor, the cover structure provides sufficient resistance that the gel pad will not be subjected to compressive forces that would squeeze the electrolytic gel from the pad. It is known and usually preferred to form the cover structures from moisture and water vapor impervious plastic materials to assist in preventing gel dry out.

It is an object of the present invention to provide a medical electrode assembly having an improved cover structure. More particularly, it is an object of this invention to provide a medical electrode assembly including an improved, low cost, disposable, low-profile pre-filled medical electrode and a cover structure therefor that helps to prevent gel dry out and also helps to prevent the gel pad from being compressed when a lead wire connector is pressed onto the connector portion of the electrode conductor.

The medical electrode assembly of this invention preferably includes a medical electrode invented by a fellow worker. It includes a gel pad securely affixed to an adhesive supporting sheet by an electrode conductor in the form of a snap fastener which extends substantially centrally through the gel pad and in which the electrode conductor and the gel pad cooperate to form a cup-like cavity for receiving the electrolytic gel. In effect, the conductor forms a base of a cup with the adjacent portions of the gel pad forming the wall of the cup. During manufacture, an electrolytic jelly or gel is injected into the cup-like cavity and some of the gel migrates into the adjacent parts of the gel pad. It is a further object of this invention to provide a medical electrode assembly utilizing such an electrode, and further having a cover designed so that when the cover and the electrode are assembled, the cover assists in partly filling the gel pad with the electrolytic gel.

The foregoing and other objects of this invention are accomplished by providing a medical electrode assembly with an electrode of the type mentioned above and with a cover structure including a planar panel portion engaging the electrode supporting sheet and having a cavity formed by a protuberance projecting from the panel portion. The bottom wall of the protuberance has a centrally located, inwardly directed plug portion that projects toward the plane of the panel. The plug portion is centered within the cavity so that an electrode centered thereover will have its conductor aligned therewith.

The outer wall of the cavity-forming protuberance is preferably in the form of a truncated cone having a maximum diameter, located at the panel portion, which is slightly larger than the diameter of the gel pad. The plug portion is also desirably formed as a truncated cone and is shaped and sized to enter into the cup-like cavity sufficiently to engage the electrolytic gel therein and to thereby displace the gel into the surrounding portions of the gel pad. The surface of the plug portion closest to the conductor is spaced slightly therefrom so that close tolerances need not be maintained in manufacture, yet when one pushes on the conductor while assembling the lead wire connector thereto, the plug portion will resist substantial movements of the conductor that might otherwise cause the gel pad to be placed under compression.

The cover for each electrode may be part of a single backing sheet or strip having plural side-by-side areas provided with cavities and forming covers for individual electrodes.

Other objects and advantages of this invention will be apparent from the following description.

BRIEF DESCRIPTION OF THE DRAWING

FIG. 1 is a perspective view taken generally from the top of an electrode assembly including at least three medical electrodes with one of the electrodes shown in exploded view and exploded from a cover or backing sheet, another of the electrodes shown partly removed from the cover or backing sheet, and the third electrode shown in assembled position on the cover or backing sheet as it would appear following manufacture and during shipping and storage. The gel is not shown in FIG. 1.

FIG. 2 is a perspective view of a portion of the electrode assembly of FIG. 1 and illustrating one of the medical electrodes which is shown exploded from its cover or backing sheet and as viewed from the bottom of the cover and the electrode. The gel is also not shown in FIG. 2.

FIG. 3 is a fragmentary cross-sectional view of the medical electrode shown in FIG. 2 taken along section line 3—3 thereof and showing the electrolytic gel as it would appear shortly after it is added during manufacture.

FIG. 4 is a cross-sectional view of the assembled electrode and the cover or backing sheet taken along line 4—4 of FIG. 1 and indicating, by heavy dash lines, the location of the gel following final assembly.

DETAILED DESCRIPTION OF THE PREFERRED EMBODIMENTS

With reference to the drawing, a medical electrode assembly in accordance with this invention is generally designated 10 and includes an elongate cover or backing sheet or strip 12 having plural, upwardly opening cavities 14, one for each of a plurality of medical electrodes that are generally designated 16. There may be any number of medical electrodes 16 forming part of the assembly 10. Often, an assembly 10 would have five electrodes and would be packaged in a suitable punch (not shown) with a second, identical electrode assembly, such being the common practice for relatively short term laboratory EKG use.

Each medical electrode 16 which was invented by a fellow worker, comprises a body member in the form of an adhesive pad or supporting sheet 18 rendered adhesive by a layer 20 of adhesive completely coating its bottom surface. The adhesive sheet 18 is centered coaxially with the cavity 14 that it overlies. Each electrode 16 further includes, in coaxial alignment with the adhesive sheet 18, a gel pad 22, an electrically conductive snap fastener stud 24, and an electrically conductive snap fastener eyelet 26 having a shank 28 pierced substantially through the center of the gel pad 22 and the supporting sheet 18. The eyelet 26 further includes a circular base flange 30 projecting from the bottom of the shank 28. When the parts are assembled, the eyelet flange 30 confronts a flange 32 forming part of the stud 24. Following conventional practice, the stud 24 and the eyelet are riveted together so that the stud 24 forms a knob suitable for attachment to a lead wire (not shown). In accordance with this invention, the stud flange 32 and the eyelet flange 30 also tightly squeeze the central portions of the adhesively coated supporting sheet 18 and the gel pad 22 therebetween.

By virtue of the fact that the center portion of the gel pad 22 is tightly squeezed against the supporting sheet 18, and because the center portion of the gel pad 22 is thus substantially reduced in thickness, a cup-like cavity 34 is produced that has a cup wall formed by the portion of the gel pad 22 encircling the eyelet flange 30, and a cup base formed by the exposed face of the eyelet flange 30.

After the parts as thus far described are assembled, an electrolyte gel 36, illustrated in FIG. 3, is added. The gel 36 may simply be inserted through a nozzle (not shown) centered over the cavity 34 while the electrode is inverted as shown in FIG. 3. The gel then migrates into portions of the gel pad 22 surrounding the gel receiving cavity 34.

The backing sheet 12 may be made from a variety of plastic materials suitable to be manufactured by thermo-vacuum forming or other inexpensive manufacturing techniques. It is preferably made from styrene or other plastic material that is relatively stiff in a thin section and substantially impervious to moisture and water vapor.

In accordance with this invention, the backing sheet 12 comprises a substantially planar panel from which the cavities 14 are recessed. Thus, as illustrated best in FIGS. 2 and 4, the cavities 14 are each formed by a protuberance generally designated 38 in the form of a truncated cone having a generally circular outer wall 40, an arcuate bottom wall 42 that curves convexly downwardly, and a centrally formed cavity plug 44 that is coaxial with the outer wall 40 and projects from the bottom wall 42 toward the plane containing the major portion of the backing sheet 12 so that, as shown in FIG. 4, when the parts are assembled, the base 46 of the cavity plug 44 confronts and is slightly spaced from the eyelet flange 30.

The protuberance 38 is formed to be of a size to be substantially filled by the gel pad 22, and may slightly compress part of the gel pad 22. The cavity plug 44 is also in the form of a truncated cone, and is sized to substantially match the diameter of the gel receiving cavity 34. As an electrode 16 is assembled onto the backing sheet 12, the assembled cavity plug 44 enters the cavity 34 and forces gel outwardly into the gel pad 22 and ultimately the gel 36 migrates throughout a substantial portion of the pad 22 as indicated by the heavy dash lines in FIG. 4. However, because the gel pad foam material provides a substantial resistance to migration of the gel, the gel typically does not migrate to the outer peripheral portions 48 of the pad 22. It may also be noted that the size of the protuberance 38 is such that its maximum diameter is only slightly greater than the diameter of the gel pad 22 so that the surrounding portions of the adhesive coating 20 are engaged with the top surface of the planar panel portion of the backing sheet 12 surrounding the cavity 14. Preferably, this top surface has a silicon release coating so that the medical electrode may be easily removed therefrom as illustrated in FIG. 1. Partly because the engagement between the adhesive coating 20 and the top surface of the backing sheet 12, and also because the gel does not migrate to the outer margins of the gel pad 22, the gel pad 22 itself forms a barrier to migration of the gel 36 to the adhesive layer 20 surrounding the gel pad 22. As a further precaution against migration of the gel 36, the backing sheet 12 may be formed with raised lips 50 at the margins of the cavities 14 to promote a good seal around the cavities 14 between the backing sheet 12 and the supporting sheet 18.

It is common practice for those using medical electrodes such as the electrode 16 to apply lead wires to all of the electrodes before they are removed from the backing sheet 12. An advantage of the construction of the protuberance 38, and particularly the manner in which the cavity plug 44 is formed, is that, when one is connecting a lead wire having a snap-on connector by pressing downwardly, the eyelet flange 38 engages the base 46 of the cavity plug 44 which thus prevents the gel pad 22 from being collapsed. Thus, a condition which might cause the gel 36 to be squeezed onto the surrounding areas of the adhesive layer 20 is avoided.

From the foregoing description of the cover or backing sheet 12, it can be seen that it comprises plural covers formed as one piece, there being a cover for each of the electrodes 16. Of course, each of the electrodes could be provided with their own separate covers and there may be cases when such would be an advantage. When an electrode 16 is placed on its cover coaxially with a cavity 14, the plug 44 is coaxial with the snap fastener eyelet 26, and accordingly centered with respect to the cup-like cavity 34. Entry of the plug 44 into the cavity 34 will displace the gel 36 substantially evenly outwardly into the surrounding portions of the gel pad 22. When the electrode 16 is fully assembled onto its cover as shown in FIG. 4, the base 46 of the plug 44 is spaced slightly from the flange 30 of the eyelet 26. When one may later attach a lead wire connector to the snap fastener stud 24 and push downwardly on the snap fastener, the plug 44 will resist substantial movements of the snap fastener parts that otherwise might permit the gel pad 22 to be placed under compression. The plug base 46 is designed not to engage the eyelet flange 30 in order to avoid critical manufacturing tolerances.

The adhesively coated supporting sheet 18 may be formed from a variety of thin, flexible plastic materials provided that they are substantially impervious to moisture and water vapor. The presently preferred material is a closed cell polyethelene foam which is inexpensive and readily available. Vinyl or other materials could also be used. In any case, the material must be substantially moisture and water vapor impervious so that it can cooperate with the backing sheet 12 to form a moisture retaining chamber for the gel pad 22 to prevent the gel 36 from drying out. As an option, the parts of the supporting sheet 18 secured to the backing sheet 12 could have perforations (not shown) extending therethrough. Such perforations would allow the adhesively engaged portions of the skin to "breathe."

The adhesive 20 may be any suitable adhesive for adhering the electrode to the skin, there being many such adhesives well known to those familiar with the manufacture of medical electrodes. A medical grade acrylic adhesive is presently preferred, but various other compositions may be used with equivalent results.

The gel pad 22 is preferably a sponge made from a highly open cell, fully reticulated polyurethane foam. This material has both resiliency and flexibility and is commonly used in the manufacture of medical electrodes. However, there may be other open cell materials which could be used. The pad 22 is initially formed as a circular disc as shown on the left side of FIG. 1. It is sized such that its outer margins are spaced inwardly from the outer margins of the supporting sheet 18, whereupon it leaves exposed a sufficiently large surface area of the adhesive coating 20 to reliably secure the electrode to the skin of a patient.

When the gel pads 22 are squeezed by the snap fastener parts during assembly, the pads 22 become rounded as shown best in FIG. 3. Furthermore, the squeezing of the center portion of the gel pad 22 causes the immediately surrounding portions to expand to a greater thickness than the original pad 22 by approximately 25 percent so as to increase the depth of the gel receiving cavity 34. Also, as illustrated in FIGS. 3 and 4, the surrounding portions of the gel pad 22 bulge or become rounded in a fashion to overlie the outer margin of the eyelet flange 30.

When the electrode is applied to the skin, the gel pad 22 is partly collapsed. The cavity 34, although reduced in size, still exists and there is an assured separation between the skin and the eyelet flange 30, such separation being considered desirable in a medical electrode as well known to those familiar with the art. However, the partly collapsed gel pad 22 still retains the electrolyte gel 36 and there is also gel 36 filling the cavity 34 so that a good, stable contact is provided between the skin and the eyelet flange 30. Furthermore, it is found that the gel 36 does not migrate to the adhesive layer 28 to interfere with the adhesion of the electrode to the skin. This is believed due in part to the fact that the gel pad 22 is not fully loaded with the gel 36. Accordingly, as the gel pad 22 is partly collapsed when the electrode 16 is applied to the skin, the gel 36 may be squeezed into the part 48 of the gel pad 22 not previously loaded with gel, but the gel is not squeezed out beyond the margins of the gel pad 22. Avoidance of fully loading the gel pad 22 with gel 36 during manufacture provides another advantage in that the amount of gel that is used in the manufacture of each electrode is not critically important. Furthermore, it is an advantage that the gel can simply be deposited in the gel receiving cavity 34 from whence it migrates into the gel pad 22.

The stud 24 and the eyelet 26 are preferably made from like conductive elements. For use in EKG monitoring, the stud 24 and the eyelet 26 may be made from stainless steel, stainless steel being inexpensive, strong, and easily formed during manufacture. The stud and the eyelet should be made from the same metal because there is a liklihood that some of the electrolytic gel 36 will be forced centrally through the eyelet shaft 28 or else will migrate around the outside of the eyelet shaft 28 into engagement with the stud 24 and, as those familiar with the art are aware, it is undesirable to have the electrolyte engage dissimilar metals. Stainless steel may be unsatisfactory for some uses, such as in an operating room, in which case the stud and the eyelet are preferably made from silver or silver-plated plastic.

Preferably the eyelet flange 30 is circular. In any case, it must be dimensioned to have a surface area sufficiently smaller than the pad 22 so that the outer margin of the pad 22 forms the cup wall as described above when the center portion of the gel pad 22 is squeezed against and thereby held in fixed relation to the adhesive supporting sheet 18.

The gel may be made from any composition compatible with the conductive material from which the eyelet 26 is manufactured, a non-chloride composition being used in the event the eyelet is made from stainless steel and a chloride composition being used in the event the eyelet is made from silver. Again, the selection of the composition is not critical to this invention, and any of several compositions known to those familiar with the art may be used.

It will be appreciated that this invention provides a low cost medical electrode assembly made from a minimum number of parts. By forming the cover or backing strip 12 with the cavities 14 for receiving the gel pad 22, and by the use of a supporting sheet 18 formed from a closed cell foam material which is substantially moisture and water vapor impervious, no additional structure is required to prevent the gel from drying out during ordinary periods of use after they are removed from their packaging.

Although the presently preferred embodiment of this invention has been described, it will be understood that various changes may be made within the scope of the appended claims.

Having thus described my invention, I claim:

1. In a disposable medical electrode assembly of the type having a pre-gelled medical electrode including a supporting sheet having an adhesive coating on one surface, a foam gel pad adjacent said one surface, a conductor comprising a snap fastener part projecting through said supporting sheet and said gel pad and squeezing a portion of said gel pad against said supporting sheet, surrounding portions of said gel pad cooperating with said snap fastener part to form a cup-like cavity, and a cover engaging said adhesively coated surface and receiving said gel pad, the improvement wherein said cover comprises a sheet construction formed to include a substantially planar panel secured to said supporting sheet by the adhesive coating thereon, said sheet construction further including a gel pad receiving cavity comprising a protuberance projecting from said panel, said protuberance having a bottom wall and a plug extending from said bottom wall toward said panel, said plug being partly received in said cup-like cavity.

2. The assembly of claim 1 wherein said sheet construction comprises a single piece of plastic.

3. The assembly of claim 1 or 2 wherein said plug is in the form of a truncated cone.

4. The assembly of claim 3 wherein said protuberance has an outer wall in the form of a truncated cone.

5. The assembly of claim 1 or 2 wherein said plug is coaxial with said protuberance.

6. The assembly of claim 1 wherein said conductor further comprises another snap fastener part adapted for connection to a lead wire, and said plug has a base remote from said bottom wall and located adjacent said first mentioned snap fastener part whereby said plug resists substantial movement of said snap fastener part when a lead wire is being attached to said another snap fastener part.

7. The assembly of claim 1 wherein said medical electrode further comprises an electrolyte gel received in said cup-like cavity and said plug is shaped and sized to force said gel outwardly into said gel pad when said medical electrode is assembled onto said cover.

8. In a disposable medical electrode assembly of the type comprising a pre-gelled electrode having a thin flexible sheet having an adhesive coating on one surface, a gel pad adjacent said one surface, a conductor including a flange squeezing a part of said gel pad against said sheet, surrounding portions of said gel pad cooperating with said flange to form a cup-like cavity, an electrolytic gel within said cavity and said gel pad, and a cover engaging said adhesively coated surface and receiving said gel pad, the improvement wherein said cover comprises a substantially planar panel surrounding said gel pad and engaging said adhesive coating, said cover being formed to provide means defining a gel pad receiving cavity including an outer wall surrounding the outer margin of said gel pad, a bottom wall spaced from said panel by a distance approximately equal to the height of said gel pad, and a plug spaced from said outer wall and extending from said bottom wall toward said conductor flange and so shaped and sized that it projects into said cup-like cavity.

9. The improvement of claim 8 wherein said plug is located in said gel pad receiving cavity coaxially with said conductor flange.

10. The improvement of claim 8 or 9 wherein said plug is in the form of a truncated cone.

11. The improvement of claim 8 wherein said conductor comprises a snap fastener part.

12. The assembly of claim 8 wherein said conductor further comprises lead wire attachment means for attachment of a lead wire thereto, and said plug has a base remote from said bottom wall and located adjacent said conductor flange whereby said plug resists substantial movement of said conductor flange when a lead wire is attached to said lead wire attachment means.

13. The assembly of claim 8 wherein said plug is shaped and sized to force said gel outwardly into said gel pad when said medical electrode is assembled onto said cover.

* * * * *

UNITED STATES PATENT AND TRADEMARK OFFICE
CERTIFICATE OF CORRECTION

PATENT NO. : 4,444,194
DATED : April 24, 1984
INVENTOR(S) : Larry R. Burcham

It is certified that error appears in the above-identified patent and that said Letters Patent is hereby corrected as shown below:

Column 3, line 35, "punch" should be --pouch--.

Signed and Sealed this

Eleventh Day of September, 1990

Attest:

HARRY F. MANBECK, JR.

*Attesting Officer*    Commissioner of Patents and Trademarks